(12) United States Patent
Walsh et al.

(10) Patent No.: US 6,297,399 B1  
(45) Date of Patent: Oct. 2, 2001

(54) INDANE COMPOUNDS WITH SMOOTH MUSCLE RELAXING AND/OR MAST CELL STABILIZING AND/OR ANTI-INFLAMMATORY ACTIVITY

(75) Inventors: John Walsh, Ballinrobe; Neil Frankish, Dublin; Helen Sheridan, Dublin; William Byrne, Dublin, all of (IE)

(73) Assignee: Venantius Limited, Dublin (IE)

(*) Notice: Subject to any disclaimer, the term of this patent is extended or adjusted under 35 U.S.C. 154(b) by 0 days.

(21) Appl. No.: 09/092,902

(22) Filed: Jun. 8, 1998

Related U.S. Application Data

(63) Continuation of application No. PCT/IE96/00082, filed on Jun. 12, 1996.

(30) Foreign Application Priority Data

Dec. 6, 1995 (IE) .......................................... 950922  
Oct. 31, 1996 (IE) .......................................... 960762

(51) Int. Cl.$^7$ .................................................. C07C 303/00
(52) U.S. Cl. ........................... 564/92; 560/255; 564/222; 564/308; 564/428; 552/8; 568/327; 568/808; 514/530; 514/621
(58) Field of Search ............................... 560/255; 564/92, 564/308, 428, 222; 568/327, 808; 552/8; 514/530, 621

(56) References Cited

PUBLICATIONS

Condensed Aromatic Compounds, vol. 70, 1969, p. 311.
Journal Association Official Analytical Chemists, 1970, 1 page.
Chemical Abstracts, vol. 79, 1973, p. 32051.
Abstract, German Patent DE2365379, 2 pages.
Indian Journal Chemistry, Sect. B, 1979, pp. 578–580.
Condensed Aromatic Compounds, vol. 93, 1980, p. 675.
Gazzetta Chimica Italiana, 1985, 1 page.
Journal Chemical Society Perkin Transactions, 1992, 2 pages.
Journal Organic Chemistry, 1990, 1 page.
Tetrahedron Letters, vol. 36, No. 7, "A novel hypervalent iodine reagent prepared from . . . ", 1995, pp. 1081–1084.
Chemical Abstracts, vol. 120, No. 17, Silverman et al, "Conformational effects on high–spin . . . ", Apr. 25, 1994, p. 216294.
Journal Am. Chem. Society, vol. 108, No. 26, Ochiai, "Tandem Michael–carbene insertion . . . ", 1986, pp. 8281–8283.
Chemical Abstracts, vol. 104, No. 25, Campagna et al, "Reduction of aldol adducts from 1,2,3 . . . ", Jun. 23, 1986, p. 224500.

(List continued on next page.)

Primary Examiner—Paul J. Killos
(74) Attorney, Agent, or Firm—Jacobson, Price, Holman & Stern, PLLC

(57) ABSTRACT

Indane compounds of general formulas (7) and (8) and their pharmaceutical use particularly to achieve smooth muscle relaxing activity and/or mast cell stabilizing activity and/or anti-inflammatory activity as described, wherein in formula (7) $R^2$ to $R^{13}$, in formula (8) $R^1$ and $R^3$ and $R^{13}$ are selected from one or more of the same or different of: H, halo, hydroxy, alkoxy, aryloxy, acetoxy, carboxy, alkyl carbonyl, hydro carbonyl, amino, amido, alkylamino, hydroxylamino, amine oxide groups, azo groups, cyano, hydrazino groups, hydrazide groups, hydrazone groups, imide groups, imino-ether groups, ureyl groups, oxime, nitro, nitrate, nitrite, nitroso groups, nitrile, heterocyclic groups containing her-etro atoms containing one or more of N, O or S, aralkyl groups, mono and polybenzoid aryl groups, substituted aryl groups, thiol, thioureyl, phenylthiol groups, sulphonic acid groups, sulphoxide groups, sulphone groups, alkyl containing 1 to 10 carbon atoms or cycloalkyl groups containing 3 to 8 carbon atoms which may saturated or unsaturated, substituted alkyl or cycloalkyl groups which may be saturated or unsaturated. X is a bond, O, or NR (wherein R is acyl, alkyl or sulphonate groups), S, SO or $SO_2$, when X is a bond any of $R^8$ and $R^{13}$; $R^8$ and $R^{12}$; $R^8$ and $R^9$ may together represent a double bond, in formula (7) any one or more of $R^2$, $^1R^2$ $R^3$, $^1R^3$; $R^9$, $^1R^9$; $R^{10}$, $^1R^{10}$; $R^{11}$, $^1R^{11}$; $R^{12}$, $^1R^{12}$ may together represent oxo, and in formula (8) any one or more of $R^1$, $^1R^1$, $R^3$, $^1R^3$; $R^9$, $^1R^9$; $R^{10}$, $^1R^{10}$; $R^{11}$, $^1R^{11}$; $R^{12}$; $^1R^{12}$ may together represent oxo.

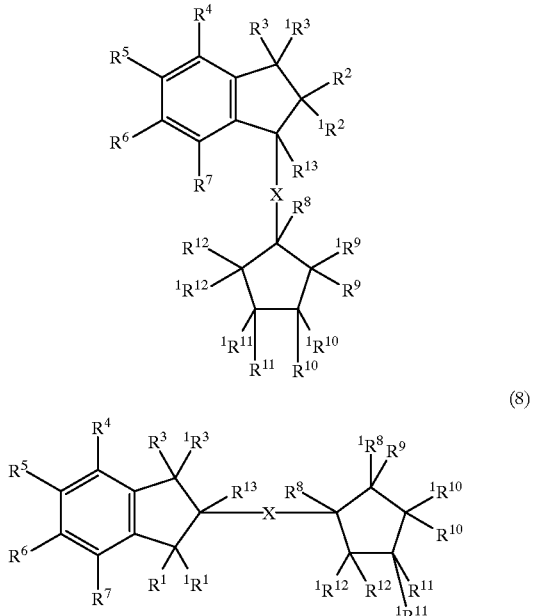

25 Claims, No Drawings

OTHER PUBLICATIONS

Chemical Abstracts, vol. 100, No. 23, Campagna et al, "Reaction of trifluoroacetic anhydride . . . ", Jun. 4, 1984, p. 191528.

Chemische Berichte, vol. 117, No. 1, Krebs et al, "Sterically Hindered alkenes. IV . . . ", 1984, pp. 277–309.

Journal Heterocyclic Chem., vol. 17, No. 7, Carotti, "Reversible cyclization of . . . ", 1980, pp. 1577–1584.

Chemical Abstracts, vol. 83, No. 7, Lagidze et al, "Steric factors affecting . . . ", Aug. 18, 1975, pp. 427–428.

Chemical Abstracts, vol. 71, No. 21, Velezheva et al, "Condensation of cyclic.beta . . . ", 1969, p. 294.

Monatshefte fur Chemie, vol. 100, No. 1, Kunz et al, "Organic Lewis acids . . . ", 1969, pp. 95–105.

Database Crossfire Neftechimijy, vol. 1, Toptschiew et al, 1961, pp. 15–20.

Journal of Medicinal Chemistry, vol. 20, No. 11, Woltersdorf et al, "(Acylarloxy) acetic acid . . . ", 1977, pp. 1400–1408.

Journal of Medicinal Chemistry, vol. 27, No. 7, Woltersdorf et al, "(Acylarloxy) acetic acid . . . ", 1984, pp. 840–845.

Chemical Abstracts, vol. 117, No. 3, Takenaka et al, "Attenuation of endothelin . . . ", Jul. 20, 1992, p. 166.

INDANE COMPOUNDS WITH SMOOTH MUSCLE RELAXING AND/OR MAST CELL STABILIZING AND/OR ANTI-INFLAMMATORY ACTIVITY

This application is a continuation of PCT/IE96/00082 filed Jun. 12, 1996.

The invention relates to indane compounds, processes for their production, compositions containing them and their pharmacological use.

According to the invention there is provided a compound of any of the formulae:

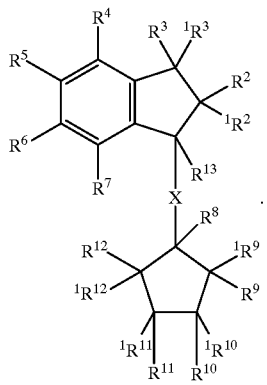

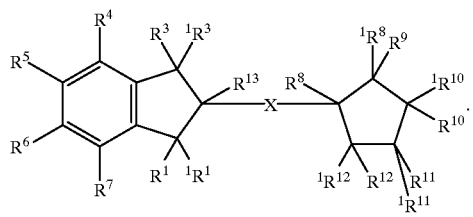

wherein
in Formula 7 $R^2$ to $R^{13}$
in Formula 8 $R^1$ and $R^3$ to $R^{13}$
are selected from one or more of the same or different of:
H, halo, hydroxy, alkoxy, aryloxy, acetoxy, carboxy, alkyl carbonyl, hydro carbonyl, amino, amido, alkylamino, hydroxylamino, amine oxide groups, azo groups, cyano, hydrazino groups, hydrazide groups, hydrazone groups, imide groups, iminoether groups, ureyl groups, oxime, nitro, nitrate, nitrite, nitroso groups, nitrile, heterocyclic groups containing hetero atoms selected from one or more of N, O or S, aralkyl groups, mono and polybenzoid aryl groups, substituted aryl groups, thiol, thioureyl, phenylthiol groups, sulphonic acid groups, sulphoxide gruops, sulphone groups, alkyl containing 1 to 10 carbon atoms or cycloalkyl groups containing 3 to 8 carbon atoms which may be saturated or unsaturated, substituted alkyl or cycloalkyl groups which may be saturated or unsaturated X is a bond, O, or NR (wherein R is acyl, alkyl or sulphonate groups), S, SO or $SO_2$
when X is a bond any of: $R^8$ and $R^{13}$; $R^8$ and $R^{12}$; or $R^8$ and $R^9$ may together represent a double bond
in formula 7 any one or more of $R^2$, $^1R^2$ $R^3$, $^1R^3$; $R^9$, $^1R^9$; $R^{10}$, $^1R^{10}$; $R^{11}$, $^1R^{11}$; $R^{12}$, $^1R^{12}$ may together represent oxo, and in formula 8 any one or more of $R^1$, $^1R^1$; $R^3$, $^1R^3$; $R^9$, $^1R^9$; $R^{10}$, $^1R^{10}$; $R^{11}$, $^1R^{11}$; $R^{12}$, $^1R^{12}$ may together represent oxo pharmacologically acceptable salts, esters, amides, solvates and isomers thereof.

In one embodiment of the invention the alkyl or cycloalkyl are substituted with one or more of the same or different of halo, oxo, hydroxy, alkoxy, aryloxy, acetoxy, carboxy, carbonyl, amino, amido, alkylamino, hydroxyamino, amine oxide groups, azo groups, cyano, hydrazino groups, hydrazide groups, hydrazone groups, imide groups, imino ether groups, ureyl groups, oxime, nitro, nitrate, nitrite, nitroso groups, nitrile, heterocyclic groups, aralkyl groups, mono and polybenzoid aryl groups, substituted aryl groups, thiol, thioureyl, phenyl thiol groups, sulphonic acid groups, sulphoxide groups and sulphone groups.

In one embodiment of the invention the heterocyclic groups are selected from herteroatoms containing one or more of N, O or S.

In Formula 7 preferably $R^4$ to $R^7$ and preferably $R^{10}$ and $R^{11}$ represent hydrogen.

In Formula 7 preferred particularly because of pharmacological activity as mast cell stabilisers are those compounds in which:
$R^2$, $^1R^2$ represent H, OH;
X is a bond;
$R^{13}$ is benzyl; and
$R^8$ and $R^9$ or $R^8$ and $R^{12}$ together represent a double bond;
or $R^3$, $^1R^3$ together represent O; and
X is NR wherein R is alkyl.

In Formula 7 preferred particularly because of pharmacological activity as anti-inflammatory agents are those compounds in which:
X represents a double bond; and
$R^2$, $^1R^2$ together represent O;
or X is NR wherein R is acyl and $R^3$, $^1R^3$ togetheer represent O.

In Formula 8 preferably $R^4$ to $R^7$ and preferably $R^{11}$ and $R^{12}$ represent hydrogen.

In Formula 8 preferred particularly because of pharmacological activity as mast cell stabilisers are those compounds in which:
$R^1$, $^1R^1$ represent H, OH.
X is a bond;
$R^{13}$ is benzyl; and
$R^8$ and $R^9$ or $R^8$ and $R^{12}$ together represent a double bond
or $R^1$, $^1R^1$ together represent O; and
X is NR wherein R is alkyl.

In Formula 8 preferred particularly because of pharmacological activity as antiinflammatory agents are those compounds in which:
X represents a double bond; and
$R^1$, $^1R^1$ together represent O
or X is NR wherein R is acyl; and
$R^1$, $^1R^1$ together represent O.

In invention relates to the compounds above for use particularly as smooth muscle relaxants and/or as mast cell stabilising agents and/or as anti-inflammatory agents.

The invention also relates to pharmaceutical compositions containing the compounds and to their use in methods of prophylaxis or treatment particularly to achieve smooth muscle relaxant activity and/or mast cell stabilising activity and/or anti-inflammatory activity.

The invention also relates to the compounds per se given in Appendix 2.

The invention also provides various processes for preparing the indane compounds as outlines in the Claims. These processes are described in more detail below.

General Reaction Procedures

1. Coupling reaction of a silyl enol either with a dimethyl acetal for the synthesis of a compound in Formula 7 and 8 wherein X is a bond.

This coupling procedure was primarily developed to couple different indanone derivatives with the cyclopentyl units. Generally, the experimental procedure was as follows.

To a stirred solution of the silyl enol ether of a particular indanone or cyclopentyl derivative corresponding dimethyl acetal of an indanone derivative or cyclopentyl derivative in dichloromethane at −78° C., was added a catalytic amount of TMS triflate. The solution was left stirring at −78° C. for 3 hours and then allowed to reach −50° C. for 1 hour. To this solution was then added a 5% solution of sodium bicarbonate. The organic layer was isolated and the aqueous layer extracted with dichloromethane. The combine organic layers were dried with sodium sulphate. After evaporation of the solvent, the crude product was passed through a plug of silica, eluting with petroleum ether 100% grading to petroleum ether:ethyl acetate, 100:4. After evaporation of the eluent the product was obtained.

2. Coupling reaction of a silyl enol ether with a cyclic-ketal of 1-indanone derivative.

Same procedure as per 1 above except that the acetal is a cyclic acetal.

3. Elimination of methanol to form α,β-unsaturated ketone for compounds in Formula 7 & 8 wherein X is a bond.

This procedure was primarily designed to synthesise α,β-unsaturated ketones from the resulting methyl ethers generated from the coupling of the silyl enol ethers and dimethyl acetals of different compounds in Formula 7 & 8 wherein X is a bond. The reaction procedure was as follows.

The required compound was dissolved in methanol and DCM, 3:1 and to this stirring solution was added triflic acid. The reaction mixture was allowed to reflux for 1 hour, after which time a precipitate formed. The solution was then cooled in an ice bath, filtered and the solid which was the respective α,β-unsaturated ketone was dried.

4. Coupling of 3-Bromoindan-1-one derivative to the silyl enol ether of cyclopentanone derivatives.

This procedure was particularly designed to couple a multitude of cyclopentanones to the 3 position of indane-1-one. None of the other synthesis that were described above to couple indanones together appeared to allow for this transformation. The success of this coupling was primarily governed by the choice of Lewis acid (TMS triflate was used) because of the presence of the potentially reactive carbonyl functional group on the 3-bromo indanone in the presence of the Lewis acids. The reaction scheme for preparing one compound of the invention is as follows:

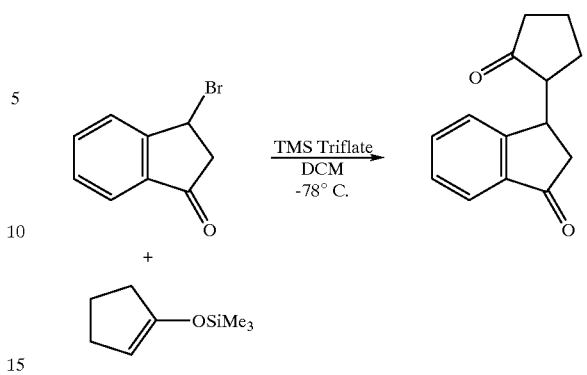

To a stirred solution of the silyl enol ether of a cyclopentanone and the corresponding 3-bromo indane-1-one in dichloromethane at −78° C., was added a catalytic amount of TMS triflate. The solution was left stirring at −78° C. for 10 mins and at room temperature for 3 hours. To this solution was then added solid sodium bicarbonate (approx. 2 g) and the solution was stirred rapidly for 10 minutes. The solution was then filtered and the filtrate was evaporated to leave a mobile oil, which was passed through a plug of silica, eluting with petroleum ether:ethyl acetate 9:2. After evaporation of the eluent, the product was obtained.

5. Coupling of cyclopentylamine derivatives to 3-bromo-indanone derivatives for compounds in formula 7 & 8 wherein X is Nitrogen.

The general reaction procedure for this reaction is as follows: cyclopentylamine derivatives were dissolved in dry DCM and to this an equivalent of 3-bromo indanone was added. The reaction solution was then cooled to 0° C. and triethyl amine was added as the tertiary base. The solution was allowed to stir at 0° C. for 3 hours. The product was purified by flash column chromatography.

6. N-Alkylation of the products from reaction procedure no. 5.

The compound was dissolved in DCM and to this was added triethylamine as the tertiary base. The desired alkylation agent was then added and the solution was allowed to stir at room temperature for 3 hours. The reaction mixture was then passed through a flash silica column and the product was eluted.

7. N-sulfonylation of the products from reaction procedure no. 5.

The compound was dissolved in DCM and to this was added p-toluenesulfonyl chloride and triethylamine. The solution was allowed to stir at 0° C. for 15 mins and then at room temperature for a further hour. Pyridine was then added to the reaction solution and the reaction was allowed to stir for a further 2 hours. The crude reaction mixture was passed through a flash silica column.

8. N-acylation of the products from reaction procedure no. 5.

The compound was dissolved in DCM and to this was added triethylamine and acetic anhydride. To this stirring solution DMAP was added. The reaction was allowed to stir at room temperature for 3 hours. To the reaction mixture was added a 2 M solution of aqueous HCl and the solvent was removed using toluene. To the crude material an aqueous solution of $NaHCO_3$ was added and the product was extracted into ether, the organic layers were combined and the solvent removed. The crude material was then passed through a flash silica column for purification.

9. β-methoxy carbonyl compounds transformation to α-alkyl and β, δ-enones for compounds in Formula 7 & 8 wherein X is a bond.

The β-methoxy carbonyl compound was dissolved in ether:ᵗbutanol (5:1) and to this the desired alkylation agent was added. To a stirring solution potassium tert-butoxide was added dropwise over a period of 30 mins. The reaction was allowed to stir at room temperature for 24 hours. An aqueous solution of ammonium chloride was added and the product was extracted into ether. The crude reaction mixture was then passed through a column of flash silica, to yield the desired product.

10. Alkylation of an enone of compounds in Formula 7 & 8 wherein X is a bond.

The required dimer was dissolved in ether:ᵗbutanol (5:1) and to this the desired alkylation agent was added. To this stirring solution, potassium tert-butoxide was added dropwise over a period of 30 mins. The reaction was allowed to stir at room temperature for 24 hours. An aqueous solution of ammonium chloride was added and the product was extracted into ether. The crude reaction mixture was then passed through a column of flash silica, to yield the desired product.

11. Lithium diisopropylamide (LDA) alkylation reactions for compounds of Formula 7 and 8 wherein X is a bond.

LDA based alkylations of α-β enone compounds has proven to have been an excellent route to 2 alkyl-β, δ enone compounds.

Generally, the experimental procedure was as follows. A three necked 100 ml round bottomed flask was oven dried and fitted with a septum and a nitrogen inlet line. The flask was then evacuated and heated with a heat gun to dry. To this flask which was filled with nitrogen was added the required dimer in dry THF. The solution was cooled to −78° C. with a liquid nitrogen/ethyl acetate bath and lithium diisopropylamide (LDA) in THF/heptane/ethylbenzene was added. After stirring for 10 minutes at −78° C., the desired organic halide was added and the solution was allowed to warm to room temperature for 3 hours under a nitrogen atmosphere. To this solution was added ether and aqueous ammonium chloride solution. The organic layer was isolated and the aqueous layer was extracted with ether. The combined organic extracts were dried over sodium sulphate and on evaporation of the solvent afforded an oil. The crude product was purified by flash column chromatography.

12. Reduction of compounds in Formula 7 & 8 wherein X is a bond with 10% Palladium on Carbon.

This procedure is particularly applicable to the reduction of the carbon—carbon double bonds of β, enone compounds in Families 7 & 8. In the case of α,β-unsaturated ketone compounds in Families 7 & 8, this method of reduction always results in both the reduction of the carbon—carbon double bond and the carbonyl of the α-β-unsaturated system. The reduction procedure was as follows.

The required compound was dissolved in ethanol and ethyl acetate. To this, 10% palladium over activated charcoal (catalytic quantities) was added and the reaction was stirred under hydrogen for 2 hours. The catalyst was removed by filtration. Evaporation of the solvent at reduced pressure afforded the crude product. The crude product was purified by flash column chromatography.

13. Reduction of compounds in Formula 7 & 8 wherein X is a bond with 10% Palladium on Carbon and concentrated aq HCl.

This procedure is particularly applicable to both the reduction of the β, carbon—carbon double bond and the ketone functional group. The reduction procedure was as follows.

The required compound was dissolved in distilled ethanol and ethyl acetate. To this, concentrated aqueous HCl 37% solution was added together with water and 10% palladium over activated charcoal (catalytic quantities) and the mixture was stirred under hydrogen for 24 hours.

The catalyst was removed by filtration and the product was extracted into ethyl acetate (3×20 ml). The crude product was purified by flash column chromatography.

14. Sodium borohydride reduction of compounds in Formula 7 & 8.

The required compound was dissolved in ethanol and sodium borohydride was added to the reaction in small portions over 10 mins. The reaction was then stirred at room temperature for 3 hours. The reaction mixture was poured onto water (20 ml) and extracted into diethyl ether (3×20 ml). Flash column chromatography over silica gel afforded the product.

15. Reduction of compounds in Formula 7 & 8 wherein X is a bond by Huang-Minlon modification reaction Hydrazine hydrate reaction.

This reduction procedure is particularly applicable to the reduction of the ketone functional group in the case of β, enones. The reduction procedure was as follows.

The required compound was dispersed in ethylene glycol. Hydrazine hydrate was added along with sodium hydroxide. The reaction was stirred at reflux for 24 hours. The reaction mixture was then cooled to room temperature and water was added and the product was extracted with ethyl acetate. The organic layer was isolated and dried over anhydrous sodium sulphate. Flash column chromatography was used to afford the pure product.

16. Cyanoborohydride reduction of compounds in Formula 7 and 8.

The required compound was dispersed in 1,2-dichloroethane at room temperature. To this solution was added zinc iodide and sodium cyanborohydride. The reaction was stirred at reflux for 20 hours. The product was added to water and extracted into ethyl acetate. Flash column chromatography (eluent:petroleum ether:ethyl acetate, 9:1) was used to isolate the pure product.

17. Reduction or isomerisation of the α,β-unsaturated double bond in dimers with 5% Palladium on carbon.

This procedure is particularly applicable to the reduction of the double bond in the case of α,β-unsaturated ketones.

The required compound was dispersed in ethanol and ethyl acetate and to this was added 5% palladium on carbon. The mixture was stirred under hydrogen for 14 hours. The palladium was removed by filtration and the solvent was removed to afford the crude reaction product. Flash column chromatography afforded the required product.

18. Wilkinsons reduction of compounds in Formula 7 and 8 wherein X is a bond.

This method of reduction was particularly effective for the selective reduction of a double bond on $R^{13}$ without reducing the double bond on the cyclopentyl ring in families 7 and 8. The reduction procedure was as follows.

The required compound was dissolved in ethanol and ethyl acetate. To this stirring solution Wilkinsons catalyst was added. The reaction was then stirred under hydrogen for 20 hours. The product was partitioned between ethyl acetate and water and the organic layer was isolated and dried with $Na_2SO_4$. The crude product was purified by flash column chromatography to yield the required product.

19. Oxime Synthesis of Compounds, in Formula 7 & 8.

This procedure is particularly applicable for the synthesis of oxime derivatives of ketonic compounds which have hydrogens α to the ketone. Generally the procedure was as follows.

The ketonic compound was dissolved in a solution of methanol:pyridine (4:1) and to this solution was then added hydroxylamine hydrochloride. Depending on the specific ketonic compound, the reaction was carried out either at room temperature or at reflux conditions.

20. O-alkylation of the Oxime of Compounds in Formula 7 & 8

This procedure is particularly applicable to O-alkylation of the oxime derivatives synthesised. Generally the procedure was as follows.

A solution of the oxime compound was dissolved in ether:tert-butanol 3:1. Benzyl bromide was generally used as the alkylating reagent and it was added to the reaction mixture. Potassium tert-butoxide 1 eq. was added dropwise to this solution at room temperature. After workup using aqueous ammonium chloride and ether the desired oxime ether was isolated after chromatography.

21. α-alkylation of O-benzyl oximes of compounds in Families 7 and 8

This procedure is particularly applicable to the α-alkylation of oxime ether derivatives.

The procedure was as follows.

A solution of the oxime ether was dissolved in dry ether and cooled to −78° C. To this solution was added n-butyl lithium followed by benzyl bromide in excess. The reaction was generally quenched with water. The product extracted with ether and purified by flush column chromatography.

22. Sulfonylation of hydroxyl functional groups in Formula 7 and 8 wherein X is a bond This procedure is particularly applicable to sulfonylation of hydroxyl groups of 2-indanol or cyclopentanol derivatives. The required hydroxylated dimer was dissolved in dichloromethane and to this solution was added methanesulfonyl chloride and N,N-diisopropylethyl amine dropwise. After stirring for 15 mins at 0° C., the reaction mixture was normally partitioned between DM and aqueous NaHCO$_3$, the organic layer was isolated washed with water, 2M aqueous HCl and finally water. Final purification of the products was by flash column chromatography.

23. Acetylation of the Hydroxyl Compounds in Formula 7 and 8

Generally the procedure was to dissolve the compound for acetylation in DCM and to use acetic anhydride as the acetylating reagent with triethylamine as base and DMAP as the acylation catalyst.

24. Hydrolysis of an Ester of Compounds of Formula 7 and 8

The required ester was dissolved in a solution of 1.45 M NaOH in THF:MeOH:H$_2$O (6:3:2), which was then refluxed. After 20 minutes, TLC showed that the hydrolysis of the ester was complete. After cooling the reaction mixture, a saturated solution of aqueous ammonium chloride, aqueous HCl (2M) and ether was added. The organic layer was isolated and the aqueous layer was extracted with ether. The combined organic extracts were dried with Na$_2$SO$_4$ and filtered. Evaporation of the solvent, left the acid.

Synthesis of 7C1 and 7C2

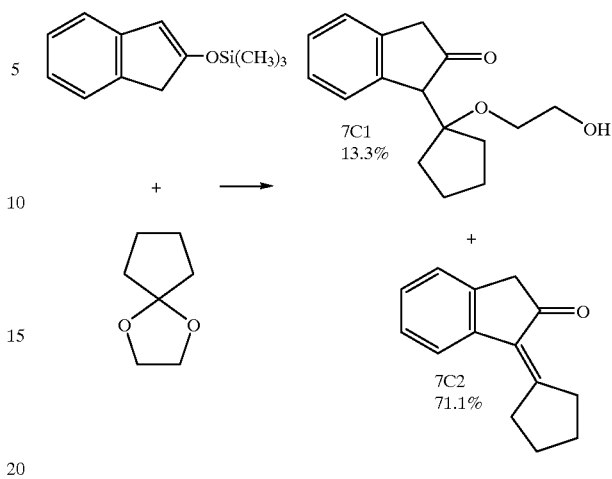

To a stirred solution of the silyl enol ether of indan-2-one (1 g, 4.9 mmol) and cyclopentanone ethylen ketal (1.13 g, 8.85 mmol) at −78° C. was added TMS triflate (25 μL). The solution was stirred at −78° C. for three hours. A 5% solution of sodium bicarbonate (20 ml approx) was added and the mixture was allowed to reach room temperature. The mixture was extracted into dichloromethane. The crude reaction mixture was passed through a flash silica column, eluting with petroleum ether:ethyl acetate (99:1), to afforded the products as a solid 7C2 (690 mg, 71.1%) and an oil 7C1 (170 mg, 13.3%).

$^1$H NMR (CDCl$_3$, 300 MHz) δ$_H$ 1.75–1.85 (4H, m, CH$_2$C$\underline{H}_2$C$\underline{H}_2$CH$_2$), 2.74 (2H, t, J=5.94 Hz, C$\underline{H}_2$CH$_2$CH$_2$CH$_2$), 3.05 (2H, t, J=6.60 Hz, CH$_2$CH$_2$CH$_2$C$\underline{H}_2$), 3.43 (2H, s, COC$\underline{H}_2$), 7.15–7.53 (4H, m, Ar-C$\underline{H}$)

$^{13}$C NMR (CDCl$_3$, 75.47 MHz) δ$_c$ 25.7, 26.2, 34.5, 34.6, 42.3 (5×$\underline{C}$H$_2$), 123.1, 124.9, 126.8, 126.9 (4×Ar-$\underline{C}$H), 128.4, 136.8, 140.8, 160.9 (2×Ar-$\underline{C}$ and 2×$\underline{C}$=$\underline{C}$), 204.2 ($\underline{C}$=O)

Synthesis of 7C3

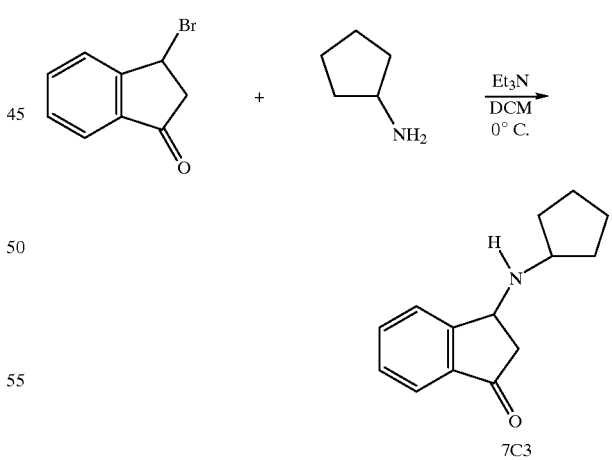

To a solution of 3-bromoindan-1-one (200 mg, 0.95 mmol) in DCM (10 ml) was added triethylamine (200 mg, 1.98 mmol) and cyclopentylamine (80 mg, 0.94 mmol). The solution was allowed to stir at 0° C. for 1 hour. The crude reaction mixture was passed through a plug of flash silica, eluting with petroleum ether:ethyl acetate, 1:1. After evaporation of the eluent 7C3 was isolated as an oil (175 mg, 85.8 %).

$^1$H NMR (CDCl$_3$, 300 MHz) $\delta_H$ 1.20–1.90 (10H, br m, 5×C$\underline{H}_2$), 2.46 & 2.53 (1H, 2×dd, J=3.3, 3.1 Hz, CH of NHCHC$\underline{H}_2$CO), 2.95 & 3.01 (1H, 2×dd, J=6.8 & 6.6 Hz, CH of NHCHC$\underline{H}_2$CO), 3.25 (1H, q, J=6.8 & 6.6 Hz, NHCHC$\underline{H}_2$CH$_2$), 4.42 & 4.44 (1H, 2×dd, J=3.1 Hz, NHC $\underline{H}$CH$_2$CO), 7.41 (1H, dt, J=1.5 & 7.0 Hz, 1×Ar-H), 7.58 & 7.60 (1H, dd, J=1.1 Hz, 1×Ar-H), 7.63 & 7.67 (1H, dd, J=0.7 & 0.9 Hz, 1×Ar-H), 7.70 & 7.72 (1H, 2×s, 1×Ar-H).

$^{13}$C NMR (CDCl$_3$, 75.47 MHz) $\delta_c$ 23.7, 23.9, 33.1, 34.0, 45.7 (5×$\underline{C}$H$_2$), 54.8, 58.3 (2×$\underline{C}$H), 123.2, 125.9, 128.5, 134.7 (4×Ar-$\underline{C}$H), 136.63, 156.4 (Ar-$\underline{C}$), 204.8 ($\underline{C}$=O).

Synthesis of 7C4

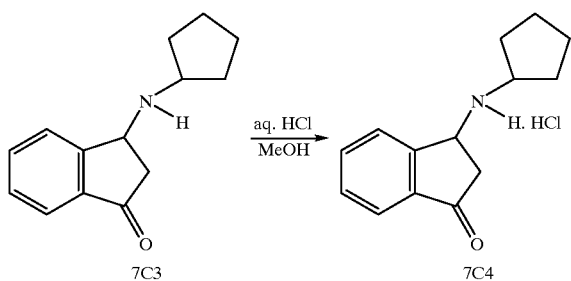

7C3 (200 mg, 0.93 mmol) was dissolved in methanol and to this was added a 2M aqueous HCl (5 ml). Toluene was then added and the solvent evaporated to dryness to afford a yellow solid. The solid was then dissolved in water and ethyl acetate was added to remove any organic impurities which were present. The water phase was extracted and was evaporated to dryness. The solid was then dissolved in the minimium amount of methanol and ethyl acetate was added. The product was then allowed to crystallise out 7C4 was then afforded as a white powder (200 mg, 85.8%).

$^1$H NMR (D$_2$O, 300 MHz) $\delta_H$ 1.65 (8H, br m, CH(C$\underline{H}_2$)$_4$), 2.04 (2H, br m, CHC$\underline{H}_2$CO), 2.83 (1H, br s, N$\underline{H}$), 3.71 (1H, t, J=6.6 Hz, C$\underline{H}$), 5.06 (1H, br s, C$\underline{H}$), 7.58 (1H, br m, 1×Ar-$\underline{H}$), 7.72 (3H, br m, 3×Ar-$\underline{H}$).

$^{13}$C NMR (D$_2$O, 75.47 MHz) $\delta_c$ 26.2, 26.3, 31.9, 32.4, 42.4 (5×$\underline{C}$H$_2$), 56.8, 60.8 (2×$\underline{C}$H), 127.0, 129,7, 133.9, 139.4 (4×Ar-$\underline{C}$H), 150.9, 150.9 (Ar-$\underline{C}$), 207.5 ($\underline{C}$=O).

Synthesis of 7C5

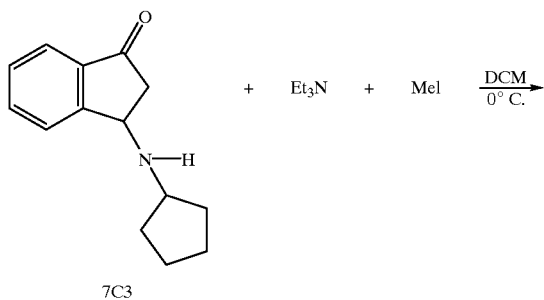

-continued

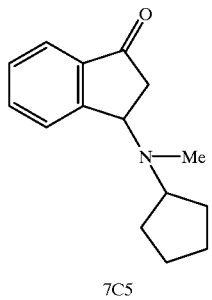

7C3 (1.0 g, 4.65 mmol) was dissolved in DCM (10 ml), the solution was then cooled to 0° C. and to the flask was added triethylamine (0.55 g, 0.76 ml, 5.45 mmol) and methyl iodide (6.60 g, 2.90 ml, 0.046 mol) were added. The reaction was allowed to stir at 0° C. for 1 hour and then the solution was allowed to come to room temperature for a further 45 mins. The crude reaction mixture was then passed through a flash silica column, eluting with petroleum ether:ethyl acetate 1:1. The product 7C5 was afforded as an oil (850 mg, 78.7%).

$^1$H NMR (CDCl$_3$, 300 MHz) $\delta_H$ 1.60–1.92 and 2.53–2.88 (11H, 2×m, 5×C$\underline{H}_2$ and C$\underline{H}$), 1.93 (3H, s, C$\underline{H}_3$), 4.78 (1H, br. t, C$\underline{H}$), 7.4–7.74 (4H, m, 4×Ar-$\underline{H}$)

$^{13}$C NMR (CDCl$_3$, 75.47 MHz) $\delta_c$ 23.8, 23.8, 31.2, 31.3, 35.8 (5×$\underline{C}$H$_2$), 33.6 ($\underline{C}$H$_3$), 59.9, 65.4 (2×$\underline{C}$H), 123.1, 126.6, 128.4, 134.7 (4×Ar-$\underline{C}$H), 137.3, 152.3 (Ar-$\underline{C}$), 211.0 ($\underline{C}$=O).

Low resolution mass spectroscopy
M$^+$229

Synthesis of 7C6

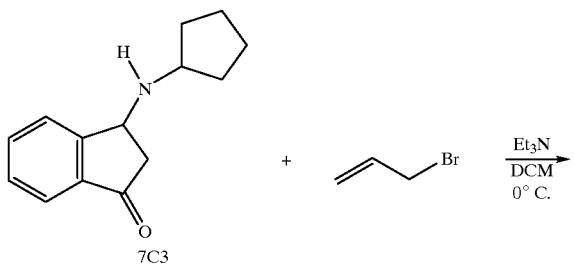

7C3 (200 mg, 0.093 mmol) was dissolved in DCM (10 ml) and to this was added triethylamine (110 mg, 0.11 mmol) and allyl bromide (1.12 g, 0.930 mmol). The solution was allowed to stir at 0° C. for 1 hour and then at room temperature for a further 2 hours. A second equivelent of both triethylamine and allyl bromide were added and the reaction was allowed to stir for a further 1 hour. The crude reaction was passed through a plug of flash silica and the product 7C6 was afforded as a yellow oil (198 mg, 83.5%).

$^{1}$H NMR (CDCl$_{3}$, 300 MHz) $\delta_{H}$ 1.43–1.87 (8H, m, 4×CH$_{2}$), 2.59–2.75 (2H, 2×q, J=4.4, 6.2 & 19.0 Hz, CHCH$_{2}$C), 2.96–3.06 (3H, m, CH$_{2}$CH=CH$_{2}$ & NCHCH$_{2}$—), 4.71 (1H, superimposed dd, J=6.2 & 4.4 Hz, CHCH$_{2}$CO), 4.95 (2H, dd, J=1.3 & 10.2 Hz, 1H of CH$_{2}$=CH), 5.09 (2H, dd, J=1.3 & 17.3 Hz, 1H of CH$_{2}$=CH), 5.76 (1H, m, CH$_{2}$=CH), 7.40 (1H, t, J=7.5 Hz, 1×Ar-H), 7.55–7.78 (3H, m, 3×Ar-H).

$^{13}$C NMR (CDCl$_{3}$, 75.47 MHz) $\delta_{c}$ 23.4, 23.8, 29.7, 31.4, 39.1, 50.9, 115.6 (7×CH$_{2}$), 58.0, 62.3 (2×CH), 122.8, 126.5, 128.2, 134.6, 137.9 (4×Ar-CH & 1×HC=CH$_{2}$), 137.3, 156.6 (2×Ar-C), 204.9 (C=O).

Synthesis of 7C7

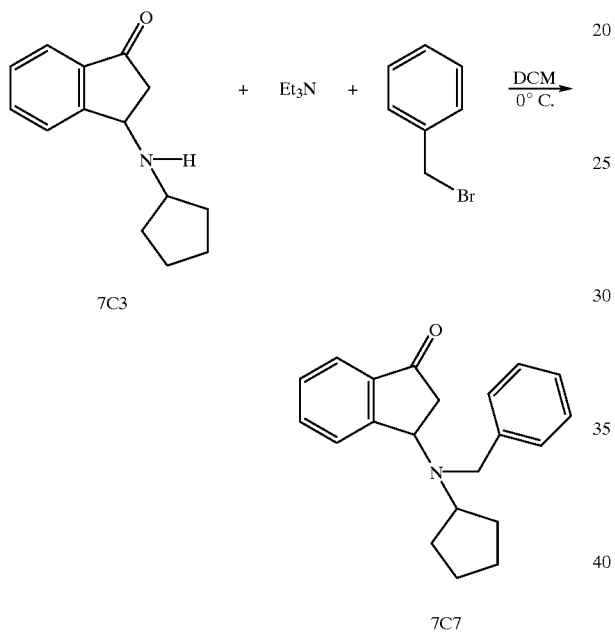

7C3 (1.0 g, 4.65 mmol) was dissolved in DCM (10 ml), the solution was then cooled to 0° C. and to the flask were added triethylamine (0.55 g, 0.76 ml, 5.45 mmol) and benzyl bromide (7.95 g, 5.53 ml, 0.046 mol). The reaction was allowed to stir at 0° C. for 1 hour and then the solution was allowed to come to room temperature for a further 45 minute. The crude reaction mixture was then passed through a flash silica column, eluting with petroleum ether:ethyl acetate 7:3. The product 7C7 was afforded as an oil (900 mg, 64.3%).

$^{1}$H NMR (CDCl$_{3}$, 300 MHz) $\delta_{H}$ 1.51 (8H, br m, 4×CH$_{2}$), 2.75 (2H, d, J=5.5 Hz, CHCH$_{2}$), 3.05 (1H, t, J=7.7 Hz, NCHCH$_{2}$CH$_{2}$), 3.56 (2H, q, J=14.5 Hz, PhCH$_{2}$), 4.68 (1H, t, J=5.3 Hz, NCHCH$_{2}$CO), 7.18–7.40 (6H, br m, 6×Ar-H), 7.60 (1H, t, J=7.3 Hz, 1×Ar-H), 7.71 (1H, d, J=14.5 Hz, 1×Ar-H), 7.76 (1H, d, J=14.3 Hz, 1×Ar-H).

$^{13}$C NMR (CDCl$_{3}$, 75.47 MHz) $\delta_{c}$ 23.4, 24.1, 29.1, 31.6, 38.9, 51.9 (6×CH$_{2}$), 57.6, 61.9 (2×CH), 122.9, 126.5, 126.8, 127.9, 128.1, 128.1, 128.1, 128.4, 134.8 (9×Ar-CH), 137.3, 140.9, 156.7 (3×Ar-C), 205.1 (C=O).

Synthesis of 7C8

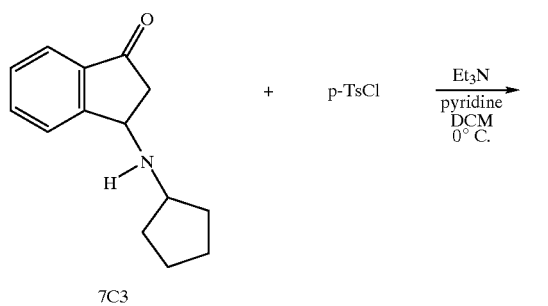

To a stirring solution of 7C3 (200 mg, 0.93 mmol) and p-toluenesulfonyl chloride (1.45 g, 7.60 mmol) in DCM (10 ml) was added triethylamine (0.09 g, 0.13 ml, 0.91 mmol). The solution was allowed to sitr at 0° C. for 15 mins. The solution was allowed to stir at 0° C. for 15 mins. The soltuion was allowed to sitr at room temperature for a further hour then to this solution was added pyridine (0.26 ml) and the reaction was allowed to stir for a further 2 hours. The crude reaction mixture was passed through a flash silica column, eluting with petroleum ether:ethyl acetate 1:4. 7C8 was isolated as a yellow solid.

Synthesis of 7C9

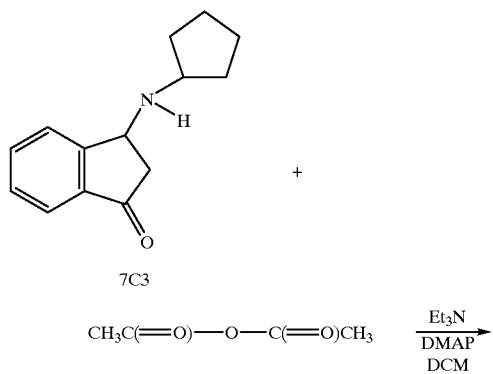

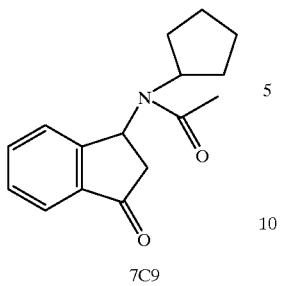

7C9

7C3 (700 mg, 0.325 mmol) was dissolved in DCM (5 ml) and to this was added triethylamine (0.657 g, 0.90 ml, 6.51 mmol) and acetic anhydride (664 mg, 0.613 ml, 6.51 mmol). Then to this stirring solution DMAP (476 mg, 0.390 mmol) was added. The reaction mixture was allowed to stir at room termperature for 3 hours. To the reaction solution was added 2 M aqueous HCl (5 ml) and 10 ml DCM. The organic layer was obtained and washed with water. To the organic was added to a 10% solution of $NaHCO_3$ (30 ml). The organic phase was collected and the aqueous layer was washed with DCM. All the organic layers were combined and dried over $Na_2SO_4$. The crude reaction was then passed through a plug of flash silica, eluting with petroleum ether 100% and grading to petroleum ether:ethyl acetate 1:4. The product 7C9 was obtained as a brownish solid (450 mg, 53.8%).

Low resolution mass spectroscopy $M^+$ 257

$^1$HNMR ($CD_3OD$, 300 MHz) $\delta_H$ 1.72–5.10 (15 H, m, $CH_2$'s, CH's and $CH_3$), 7.4–7.85 (4 H, m 4×Ar—CH)

Synthesis of 7C10

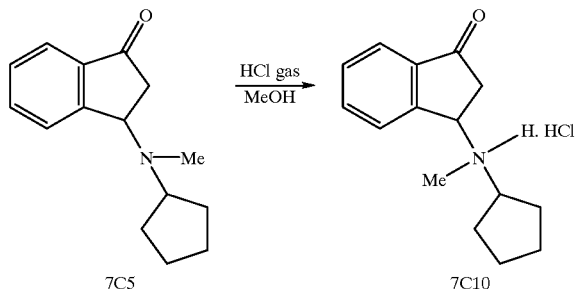

Compound 7C5 (100 mg) was dissolved in dry methanol (5 ml), dry HCl gas was bubbled through the solution of 5 mins. The methanol was then evaporated off and a white solid remained. The solid was then partioned between water and ether. The aqueous layers were combined and evaporated to dryness. The white solid 7C10 which remained was dried on the vac line (95%).

Synthesis of 8Cl

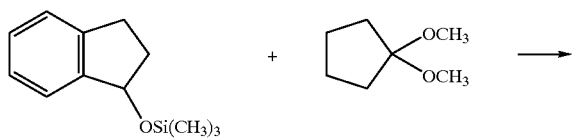

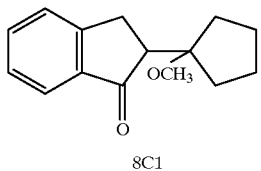

8C1

The dimethyl acetal of cyclopentanone (1 g, 7.7 mmol) and silyl enol ether of indan-1-one (1 g, 4.9 mmol) were dispersed in DCM (5 ml) and cooled to −78° C. To this solution was added TMS triflate (25 μl) in DCM (1 ml) and the solution was stirred for 2 h. Solid sodium bicarbonate (approx 1 g) was added and the mixture was allowed to reach room temperature. The product was purified by flash chromatography eluent petroleum spirits bp 40–60° C.:ethyl acetate (99:1). Yield (1.09 g, 96.8%)

8C1

$^1$H NMR ($CDCl_3$, 300 MHz) $\delta_B$ 1.31–1.72 (6 H, m, 3×$CH_2$), 1.81–1.90 (1 H, m, CH of $CH_2$), 1.92–2.20 (1 H, m, CH of $CH_2$), 2.91 (1 H, dd, J=2.6 Hz, J=5.9 Hz, $CHCH_2$), 3.02 (3 H, s, $OCH_3$), 3.11 (2 H, t, J=5.49 Hz, $CHCH_2$), 7.21 (1 H, dt, J=7.14 Hz and 0.87 Hz, Ar—H), 7.33 (1 H, d, J=7.68 Hz, Ar—H), 7.44 (1 H, dt, J=7.68 and 1.08 Hz, Ar—H), 7.59 (1 H, d, J=7.68 Hz, Ar—H)

$^{13}$C NMR ($CDCl_3$, 75.47 MHz) $\delta_C$ 23.3, 23.7, 29.4, 33.1, 33.3 (5×$CH_2$), 49.7 (CH), 51.2 ($OCH_3$), 87.8 (qC), 123.3, 126.1, 126.8, 134.3 (4×Ar—CH), 137.4, 153.4, (2×Ar—C), 206.1 (C=O)

Synthesis of 8C2

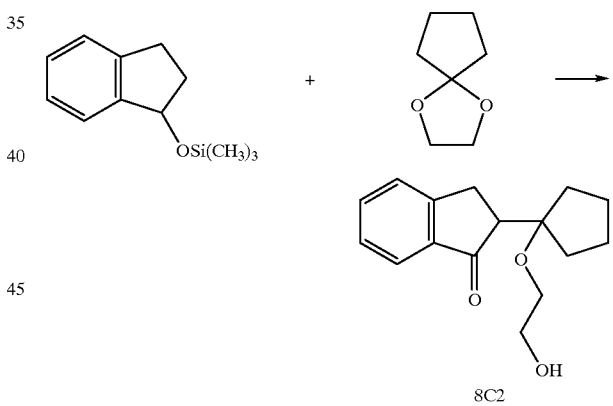

8C2

To a stirred solution of the silyl enol ether of indan-1-one (1 g, 4.9 mmol) and cyclopentanone ethylene ketal (1.13 g, 8.85 mmol) at −78° C. was added TMS triflate (25 μl). The solution was stirred at −78° C. for three hours. A 5% solution of sodium bicarbonate (20 ml approx) was added and the mixture was allowed to reach room temperature. The mixture was extracted into dichloromethane. The crude reaction mixture was passed through a flash silica column, eluting with petroleum ether:ethyl acetate (99.1), to afford the product as an oil (830 mg, 65.1%).

$^1$NMR ($CDCl_3$, 300 MHz) $\delta_B$ 1.35–1.79 (8 H, m 4×$CH_2$), 2.96–3.10 (3 H, m, $OCH_2$, $CH_2CH$), 3.31–3.34 (2 H, m, $COCCH_2$), 3.50–3.60 (3 H, m, $CH_2OH$), 7.22 (1 H, dt, J=7.02 and 0.9 Hz, Ar—H), 7.31 (1 h, d, J=7.44 Hz, Ar—H), 7.41 (1 h, dt, J=7.05 and 0.87 Hz, Ar—H), 7.52 (1 H, d, j=7.57 Hz, Ar—H)

$^{13}$C NMR (CDCl$_3$, 75.47 MHz) δ$_C$ 23.2, 23.5, 29.6, 33.2, 33.5 (5×CH$_2$), 50.4 (COCH), 61.6, 63.3 (2×CH$_2$), 87.7 (qC), 123.3, 125.9, 126.9, 134.4 (4×Ar—CH), 137.1, 153.3 (2×Ar—C), 206.5 (C=O)

Synthesis of 8C3

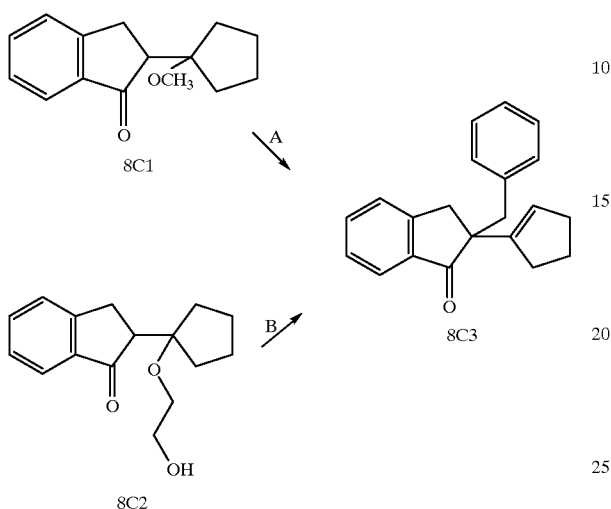

Synthesis of 8C4

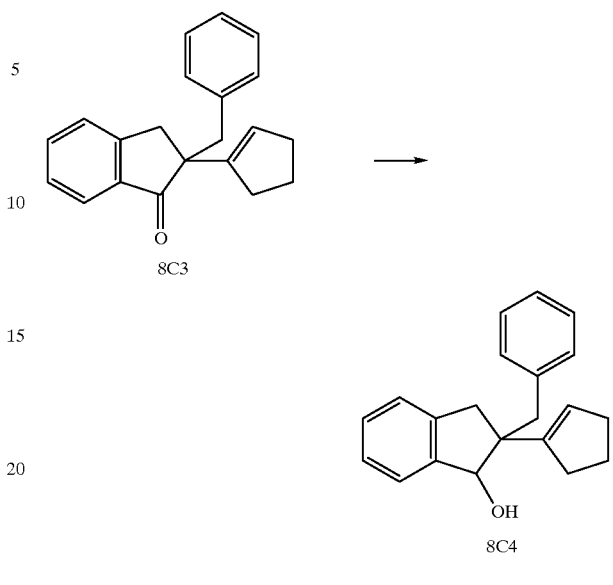

Method A

8C1 (500 mg, 2.2 mmol) was dissolved in ether (10 ml) and $^t$butanol (2 ml), to this benzyl bromide (500 mg, 0.33 ml, 2.88 mmol) was added. To this stirring solution, potassium tert-butoxide (320 mg, 2.88 mmol) in $^t$butanol (10 ml) was added dropwise over 20 minutes. The solution was allowed to stir for 3 hours. To this solution saturated aqueous ammonium chloride solution (20 ml) was added and the organic phase was extracted with ether (2×50 ml). The organic layers were combined, dried and the crude product was purified by flash column chromatography to afford 8C3 (457 mg, 72.6%).

Method B

8C2 (500 mg, 1.9 mmol) was dissolved in ether (10 ml) and $^t$butanol (2 ml), to this benzyl bromide (500 mg, 0.33 ml, 2.88 mmol) was added. To this stirring solution, potassium tert-butoxide (320 mg, 2.88 mmol) in $^t$butanol (10 ml) was added dropwise over 20 minutes. The solution was allowed to stir for 3 hours. To this solution saturated aqueous ammonium chloride solution (20 ml) was added and the organic phase was extracted with ether (2×50 ml). The organic layers were combined, dried and the crude product was purified by flash column chromatography to afford 8C3 (220 mg, 40.5%).

$^1$H NMR (CDCl$_3$, 300 MHz) δ$_B$ 1.85 (2 H, t, J=7.47 Hz, CHCH$_2$CH$_2$), 2.32–2.41 (4 H, m, 2×CH$_2$), 3.13 (1 H, d, J=13.59 Hz, 1 H of COCCH$_2$), 3.21 (2 H, s, CH$_2$—Ar), 3.37 (1 H, d, J=13.59 Hz, 1 H of COCCH$_2$), 5.62 (1 H, s, CCHCH$_2$), 7.12–7.17 (5 H, m, Ar—H), 7.24–7.29 (2 H, m, Ar—H), 7.44–7.48 (1 H, t, J=7.44 Hz, Ar—H), 7.81 (1 H, d, J=7.56 Hz, Ar—H)

$^{13}$C NMR (CDCl$_3$, 75.47 MHz) δ$_C$ 23.2, 32.2, 32.2, 36.6, 40.6 (5×CH$_2$), 56.6 (qC), 124.0, 125.9, 126.1, 126.4, 127.0, 127.8, 127.8, 129.9, 129.9, 134.5 (9×Ar—CH, 1×C=CH), 135.8, 137.5, 144.3, 152.6, (3×Ar—C, 1×C=CH), 207.0 (C=O)

8C3 (200 mg, 0.7 mmol) was dissolved in ethanol and ethyl acetate (2.1, 9 ml) and sodium borohydride (300 mg, 0.789 mmol) was added to the reaction in small portions over 10 minutes. The reaction was stirred at room temperature for 3 hours. The reaction mixture was poured onto water (20 ml) and ectracted into diethyl ether (3×20 ml). Flash column chromatography over silica gel eluent:petroleum ether (b.p. 40–60° C.):ethyl acetate, 98:2) afforded 8C4 (190 mg, 94.3%).

$^1$H NMR (CDCl$_3$, 300 MHz) δ$_H$ 1.02–1.09 (2 H, m, CHCH$_2$CH$_2$), 2.03–2.13 (2 H, m, CH$_2$), 2.21–2.65 (5 H, m, 2×CH$_2$, 1×OH), 2.89–3.21 (2 H, m, CH$_2$), 4.92 and 5.15 (1 H, 2×s, each 0.5 of CHOH), 5.33 and 5.57 (1 H, 2×s, each 0.5 of C=CH), 7.10 (2 H, dt, J=1.32 and 9.27 Hz, 2×Ar—H), 7.27–7.58 (7 H, m, 7×Ar—H)

$^{13}$C NMR (CDCl$_3$, 75.47 MHz) δ$_C$ 23.4, 23.5, 32.1, 32.3, 33.2, 33.3, 35.9, 37.2, 38.0, 40.8 (5×CH$_2$), 55.1, 55.4 (qC), 80.7, 81.8 (CHOH), 123.8, 124.5, 124.8, 125.3, 125.6, 125.9, 126.4, 126.5, 127.3, 127.5, 127.5, 127.8, 128.4, 130.1, 130.1, 130.2, 130.2 (9×Ar—CH), 126.1, 129.3 (C=CH), 138.2, 138.8, 140.7, 142.3, 143.6, 144.0, 145.3, 147.1 (3×Ar—C, 1×C=CH)

Synthesis of 8C5

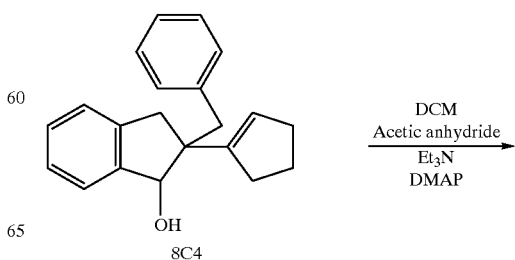

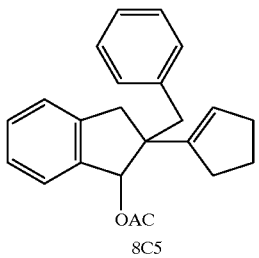

8C5

8C4 (100 mg, 0.3 mmol) was dispersed in DCM (2 ml) and triethyl amine (0.15 g, 0.2 ml). To this acetic anhydride (0.45 ml) and DMAP (0.1 g) was added. The mixture was stirred at room temperature for 1 hour. Flash column chromatorgaphy was used to isolate the product as a diastereomeric mixture 8C5 (0.013 g, 91.0%).

$^1$H NMR (CDCl$_3$, 300 MHz) $\alpha_H$ 1.87 (3 H, s, COCH$_3$), 1.94–1.91 (2 H, m, CH$_2$), 2.29–2.42 (4 H, m, 2×CH$_2$), 2.75–2.80 (2 H, m, CH$_2$), 2.95–3.15 (2 H, m, CH$_2$), 5.18 and 5.24 (1 H, 2×s, CHOCO), 6.01 and 6.21 (1 H, 2×s, C=CH), 6.70–7.31 (9 H, m, 9×Ar—H).

$^{13}$C NMR (CDCl$_3$,75.47 MHz) $\sigma_c$ 22.9, 23.7, 31.7, 31.8, 32.4, 32.5, 37.6, 39.3, 39.8 (5×CH$_2$), 53.3, 53.4 (qC), 81.6 (CHOCO), 124.0, 124.4, 124.7, 125.5, 125.7, 126.0, 126.1, 126.3, 126.7, 127.1, 127.4, 128.1, 128.7, 129.5, 129.7 (9×Ar—CH & 1×C=CH), 137.1, 138.1, 140.4, 140.5, 141.8, 143.4, 144.3, 145.4 (2×Ar—C & C=CH), 169.8, 169.9 (C=O).

Synthesis of 3-azido-indan-1-one

To a stirring solution of 3-Bromo indan-1-one (400 mg, 1.90 mmol) in DMF (5 ml) was added sodium azide (1.98 g, 0.03 mol). The reaction was allowed to stir at room temperature for 15 mins. The product was partitioned between water (10 ml) and ether (10 ml). The ether layers were combined and the crude reaction mixture was passed through a plug of flash silica, eluting with petroleum ether:ethyl acetate (9:1). The product was isolated as an orange oil (283 mg, 86%).

$V_{max}$/cm$^{-1}$2101 (N$_3$).

$^1$H NMR (CDCl$_3$, 300 MHz) $\delta_H$ 2.54 (1H, dd, J=3.1 Hz & 18.9 Hz, CH of CH$_2$), 2.98 (1H, dd, J=7.4 Hz & 19.0 Hz, CH of CH$_2$), 5.0 (1H, dd, J=3 Hz & 7.4 Hz, CHN$_3$), 7.39–7.64 (4H, m, 4×Ar—H).

$^{13}$C NMR (CDCl$_3$, 75.47 MHz) $\delta_C$ 43.0 (CH$_2$), 57.5 (CH), 123.3, 125.8, 129.6, 135.1 (4×Ar—CH), 136.2, 151.0 (2×Ar—C), 201.3 (C=O).

It will be appreciated that the compounds include pharmacologically acceptable salts, esters, isomers and solvates thereof. One example of a possible ester is a salicylate in at least one and possibly several suitable positions on the compound. This opens up the possibility of a combination therapy using an indane compound and aspirin in a single molecule. The weight ratio of the base indane compound to aspirin may be selected by providing a salicylate at a number of selected positions on the compound.

It will be appreciated most of the compounds have one or more chiral centres and hence exist as a pair of enantiomers or as a mixture of diastereomers. This may have an effect on the pharmacological properties.

It will be appreciated that for pharmaceutical purposes the active compounds may be formulated in any desired form using any suitable excipients and/or carriers. For example, particularly in the case for use to achieve antiinflammatory activity the compound may be formulated in a pharmaceutical composition suitable for topical/transdermal application.

PHARMACOLOGY

Introduction

The compounds according to the invention have potent mast cell stabilising activity, smooth muscle relaxing activity and anti-inflammatory activity. Such compounds are, therefore, potential anti-asthmatic agents with bronchodilator activity. The mast cell stabilising activity of the compounds suggests their potential use in the treatment of allergic rhinitis, allergic conjunctivitis and other anaphylactic or allergic conditions. The anti-inflammatory activity may have applications in gout, rheumatic diseases, ankylosing spondylitis, polymyalgia rheumatica, temporal arteritis, polyarteritis nodosa, polymyositis and systemic lupus arteriosis and other inflammatory conditions. Topical applications may include: atopic excema, weeping excemas psoriasis, chronic discoid lupus erythematosus, lichen simplex chronicus, hypertrophic lichen planus, palmar plantar pustulosis. They may also have potential in the treatment of some malignant diseases and as immunosuppressants.

The smooth muscle relaxing activity of the compounds may have potential in the treatment of hypertension and peripheral vascular disease, such as intermittent claudication and Reynaud's syndrome, as well as other cardiovascular disorders, such as congestive heart failure, angina pectoris, cerebral vascular disease and pulmonary hypertension. Such compounds are also indicated for potential use in the treatment of certain disorders of the gastro-intestinal tract, such as diverticular disease and irritable bowel syndrome. Similarly, these compounds may have potential as agents for the treatment of disorders of the genito-urinary tract, such as premature labour, incontinence, renal colic and disorders associated with the passage of kidney stones. Members of this group of compounds may also have potential as diuretics, analgesics, antipyretics, local anaesthetics, central nervous system depressants and hypoglycaemic agents.

The compounds were assessed for their ability to stabilise mast cell membranes in vitro. Mast cells treated with the compounds and un-treated mast cells were stimulated to release histamine. A reduction in histamine release by the treated cells compared to the un-treated cells indicates stabilisation of the membrane. The compounds were assessed for their ability to relax smooth muscle in vitro. Intestinal smooth muscle was stimulated to contract, using calcium chloride, and subsequently treated with the compounds, relaxation of the contraction was measured for each compound. The effects of the compounds were also studied on relaxation of guinea-pig tracheal muscle. In the mouse ear oedema test, compounds were administered topically prior to inducing inflammation by the topical application of arachidonic acid. The width of the ear was determined both before and after treatment as an index of oedema.

There follows protocols of each of these assays and a summary of the results.

Abbreviations

| | |
|---|---|
| BSS | buffered salt solution |
| $CaCl_2$ | calcium chloride |
| $CO_2$ | carbon dioxide |
| DMSO | dimethyl sulphoxide |
| DSCG | disodium cromoglycate |
| $cH_2O$ | distilled water |
| HCl | hydrochloric acid |
| HEPES | N-2-hydroxyethylpiperazine-N-2-ethanesulphonic acid |
| KCl | potassium chloride |
| $\lambda_{em}$ | emission wavelength |
| $\lambda_{ex}$ | excitation wavelength |
| M | Molar |
| $MgCl_2$ | magnesium chloride |
| min | minutes |
| ml | microliters |
| mM | milli-molar |
| NaCl | sodium chloride |
| $NaHCO_3$ | sodium hydrogen carbonate |
| $NaH_2PO$ | sodium hydrogen phosphate |
| NaOH | sodium hydroxide |
| $O_2$ | oxygen |
| oPT | o-phthaldialdehyde |
| S.E.M. | standard error of mean |
| w/v | weight per volume |
| v/v | volume per volume |

Methods

Histamine Release Assay

The buffered salt solution (BSS) was prepared in advance (NaCl 137 mM; KCl 2.7 mM; $MgCl_2$ 1.0 mM; $CaCl_2$ 0.5 mM; $NaH_2PO_4$ 0.4 mM; Glucose 5.6 mM; HEPES 10 mM). This was dispensed into test tubes and heated to 37° C., each test tube contained 4.5 ml BSS. The solvent blank was supplemented with 0.5% (v/v) dimethyl sulphoxide (DMSO) or 0.5% (v/v) distilled water ($dH_2O$). The two positive controls were supplemented with 0.5% (v/v) distilled water ($dH_2O$). The two positive controls were supplemented with 0.5% (v/v) $dH_2O/2\times10^{-5}M$ disodium cromoglycate (DSCG) and 0.5% (v/v) DMSO)/$2\times10^{-5}M$ DSCG. The test compounds' incubation tubes contained $2\times10^{-5}M$ test compound/0.5% (v/v) DMSO. The basal release, maximum release and total histamine content incubation tubes contained no additions.

Female Wistar rats (200–300 g) were killed in an atmosphere of saturated $CO_2$. Pre-warmed BSS (10 ml) was injected i.p. and the abdomen was massaged for 3 min. The BSS, with suspended mast cells and other cells, was aspirated following a mid-line incision. The aspirate was centrifuged for 5 min at 400 g and the supernatant removed. The cells were re-suspended in BSS, at 4° C., and centrifuged as before. The cells were washed in this manner a total of three times. Following the final wash, the pelleted cells were stored at 4° C., for use as soon as possible.

The cells were re-suspended in 7 ml BSS. From this, 0.5 ml aliquots were transferred to each of the incubation tubes. After 10 min at 37° C., with gentle agitation, Compound 48/80 was added to a final concentration of 2 mg/ml, in order to stimulate histamine release. The cell stimulation was stopped after 2 min by the addition of 0.5 ml ice cold BSS, the incubation tubes were transferred to an ice bath. The cell suspensions were centrifuged for 5 min at 400 g. The 'total histamine content' tube was placed at 100° C. for 2 min prior to centrifugation. The supernatants were retained for histamine assay.

To 2 ml of supernatant from each tube was added 0.4 ml of 1M NaOH and 0.1 ml oPT (1% (w/v) in methanol). This was incubated at room temperature for 4 min. The reaction was stopped by the addition of 0.2 ml of 3M HCl. The supernatant from each incubation tube was assayed in duplicate and run simultaneously with a standard curve in the range 0–1000 ng/ml. The presence of the fluorescent product of the reaction was measured using a Shimadzu RF-1501 spectrofluorophotometer set at $\lambda_{ex}$=360 nm, $\lambda_{em}$=450 nm.

Each drug was tested on at least five animals (n=5). The results were expressed as a percentage of maximum, compound 48/80 induced, histamine release in the solvent blank sample. Each drug was compared to DSCG on the same tissues. The basal histamine release in untreated cells was noted, expressed as a percentage of the total histamine content of the cells in suspension. The maximum histamine released by the cells in response to compound 48/80, in the relevant solvent blank sample, was expressed in the same manner. Overall, the mean basal release was 9.60% (S.E.M.=1.02) of total histamine content of the cells (n=55). The maximum stimulated histamine release was 67.38% (S.E.M.=2.90) in the presence of 0.5% (v/v) $dH_2O$ and 54.87% (S.E.M.=2.69) in the presence of 0.5% (v/v) DMSO of total histamine content of the cells (n=55).

Smooth Muscle Effects

Guinea pigs (350 g approx.), of either sex, were killed in an atmosphere of saturated $CO_2$. The abdomen was opened by a mid-line incision and the small intestine was removed. The trachea was removed and sectioned between the cartilage rings, which were then split through.

Segments of ileum (1–1.5 cm) were suspended in a high potassium, no calcium Krebs buffer (NaCl 160.4 mM; KCl 45 mM; $MgCl_2$ 0.54 mM; $NaH_2PO_4$ 0.89 mM; $NaH_2CO_3$ 24.9 mM: Glucose 11.1 mM). Tracheal sections were suspended in normal Krebs buffer (NaCl 236.5 mM; KCl 4.7 mM; $CaCl_2$ 2.5 mM; $MgCl_2$ 0.54 mM; $NaH_2PO_4$ 0.89 mM; $NaHCO_3$ 24.9 mM; Glucose 11.1 mM). The solutions were maintained at 37° C. by a jacketed organ bath and gassed with 95% $O_2$ and 5% $CO_2$. The tissues were anchored by thread to the bottom of the organ bath and suspended from force displacement transducers under a resting tension of 1 g approx. in the case of ileum and 4 g approx. in the case of trachea. Isotonic contractions were recorded using a MacLab/4e system in conjunction with the Chart 3.3.1 software package. Surplus tissue was stored at 4° C. in Krebs buffer, for a maximum of 48 hours.

Four segments of tissue were suspended and observed concurrently. Contractions of ileum were initiated by the addition of 25 μl of 1M $CaCl_2$ (a final concentration of 2.5 mM). The contractions stabilized with time, 10–15 min, and could be maintained for up to 45 min. from the addition of the $CaCl_2$. The tracheal sections were allowed to develop spontaneous resting tension over a period of 30 mins.

Stock solutions of drug were prepared at $10^{-3}M$ in 50 % (v/v) DMSO. These were diluted to give; $10^{-4}M$ in 5% (v/v) DMSO and $10^{-5}M$ in 0.5% (v/v) DMSO. In cases of poor solubility, the $10^{-3}M$ stock was made up in higher concentrations of DMSO. Solvent 'blank' solutions were prepared containing 50%, 5% and 0.5% (v/v) DMSO (or as appropriate). A cumulative dose-response assay was carried out in the range $5\times10^{-8}M$ to $10^{-5}M$. A second cumulative dose-response assay was carried out using DMSO 'blank' solutions only.

Each drug was tested, in duplicate, on at least three different animals (n=3). The results were expressed as percentage inhibition of the $CaCl_2$ induced contraction in the case of ileal tissue and percentage relaxation in the case of tracheal tissue, for each tissue, at each concentration of drug in DMSO. The effect of DMSO, for each tissue at each concentration, was subtracted from the effect of the drug in DMSO, to give the effect of the drug alone. A log dose vs. response curve was plotted for each drug using the mean and the standard error of the mean for the cumulated results.

In vivo Inflammation

The mouse ear oedema model was performed using Laca mice (25–35 g), of either sec. The animals were sedated with fentanyl/fluanisone (Hypnorm, Janssen). One ear was treated by the topical application of one of a range of test compounds, indomethacin or hydrocortisone (all at 300 μg per ear in acetone). After 30 min., oedema was induced by the topical application of arachidonic acid (10 μl at 0.4 g/ml in acetone). The width of each ear was measured, both before and 60 min. after the induction of oedema, using a micrometer screw gauge. Ear oedema was calculated by comparing the ear width before and after induction of oedema and expressed as percentage normal.

Results

Mast Cell stabilising activity

The findings of the histamine release and the smooth muscle effect assays are summarised in the accompanying tables of results. The results indicate that these compounds show a wide variety of smooth muscle relaxing and mast cell stabilising activity, and that these two effects are not related (i.e. a good mast cell stabiliser is not necessarily a good smooth muscle relaxant and vice versa).

arachidonic acid (all n=4 except 8C4 (n=5) and solvent controls (n=8)). The results suggest that anti-inflammatory activity is not linked to mast cell stabilising activity.

| Compound | Mean % | SEM |
|---|---|---|
| Dexamethasone | 37.9 | 8.5 |
| Indomethacin | 39.6 | 5.8 |
| 7C2 | 48.3 | 16.3 |
| 7C9 | 10.5 | 6.2 |
| 8C4 | 80.3 | 15.7 |
| Control | 78.8 | 15.2 |

The invention is not limited to the embodiments hereinbefore described which may be varied in detail.

APPENDIX 1

LIST OF ABBREVIATIONS USED

| | |
|---|---|
| $AlCl_3$ | aluminium chloride |
| aq | aqueous |
| b.p. | boiling point |
| $BrCH_2C_6H_4CO_2CH_3$ | methyl 4-(bromomethyl)benzoate |
| $BrCH_2CO_2CH_3$ | bromomethyl acetate |
| BSS | buffered salt solution |
| $CaCl_2$ | calcium chloride |
| $C_2H_5I$ | iodoethane |
| $C_6H_3(CH_3)Br(CH_3)$ | bromo-m-xylene |
| $C_6H_5CH_2Br$ | benzyl bromide |
| $CDCl_3$ | chloroform-d |
| $CF_3SO_3Si(CH_3)_3$ | trimethylsilyl trifluoromethanesulfonate |

| | Percentage inhibition of: | | | | | |
|---|---|---|---|---|---|---|
| | CaCl2 Induced Contractions (±S.E.M.) | | | Spontaneous Tone (±S.E.M.) | | Histamine Release (±S.E.M.) |
| Conc. (M) | ileum | $3 \times 10^{-6}$ | $10^{-6}$ | trachea $3 \times 10^{-6}$ | $10^{-6}$ | $2 \times 10^{-6}$ |
| 7C3 | | | | | | 83.0 ± 1.23 |
| 7C4 | | | | 0.80 ± 1.59 | -5.03 ± 2.55 | 25.66 ± 3.70 |
| 7C5 | | | | | | 88.02 ± 2.26 |
| 7C6 | | 2.51 ± 2.18 | 12.09 ± 3.11 | -0.38 ± 2.11 | -7.75 ± 3.89 | 83.66 ± 3.42 |
| 7C7 | | | | | | 83.16 ± 4.26 |
| 7C8 | | | | | | 40.26 ± 5.39 |
| 7C9 | | 11.63 ± 4.91 | 15.36 ± 4.62 | -0.79 ± 1.53 | 2.39 ± 2.78 | -0.90 ± 5.40 |
| 7C10 | | | | | | 90.80 ± 2.62 (n = 4) |
| 8C1 | | | | | | 4.02 ± 2.73 |
| 8C4 | | | | | | 63.55 ± 9.85 |

Inflammation

Mouse Ear Oedema Model

Responses of the mouse ear to single doses of a range of compounds compared to the response to indomethacin and dexamethasone, each at a dose of 300 μg per ear administered topically 30 min. prior to administration of 400 μg of arachidonic acid. Values are expressed as the percentage increase in ear thickness 1 hour after administration of

APPENDIX 1-continued

LIST OF ABBREVIATIONS USED

| | |
|---|---|
| | (TMS triflate) |
| $CH(OCH_3)_3$ | trimethylsilyl orthoformate |
| $CH_3C_6H_4SO_3H.H_2O$ | p-toluenesulfonic |

APPENDIX 1-continued

LIST OF ABBREVIATIONS USED

| | |
|---|---|
| $CH_3I$ | iodomethane |
| $ClCH_2CH_2COCl$ | β-chloropropionylchloride |
| $CO_2$ | carbon dioxide |
| $CS_2$ | carbon disulfide |
| $[(C_6H_5)_3P]_3RhCl$ | tris(triphenylphosphine)rhodium(1) chloride (wilkinsons catalyst) |
| $[(CH_3)_3CO]_3Al$ | aluminium tri-tert-butoxide |
| DCM | dichloromethane |
| $dH_2O$ | distilled water |
| DMSO | dimethyl sulphoxide |
| DSCG | disodium cromoglycate |
| $Et_2O$ | ether |
| $Et_3N$ | triethylamine |
| EtOAc | ethyl acetate |
| EtOH | ethanol |
| $H_2C=CHCH_2Br$ | allyl bromide |
| $H_2NNH_2.H_2O$ | hydrazine hydrate.monohydrate |
| $H_2O$ | water |
| $H_2SO_4$ | sulphuric acid |
| HCl | hydrochloric acid |
| HEPES | N-2-hydroxyethylpiperazine-N-2-ethanesulphonic acid |
| $HOCH_2CH_2OH$ | ethylene glycol |
| IR | infra red |
| KCl | potassium chloride |
| LDA | lithium diisopropylamide |
| M | Molar |
| $MgCl_2$ | magnesium chloride |
| min | minutes |
| μl | microliters |
| mM | milli-molar |
| m.p. | melting point |
| $N_2$ | nitrogen |
| $NaBH_4$ | sodium borohydride |
| NaCl | sodium chloride |
| $NaCN(BH_3)$ | sodium cyanoborohydride |
| $NaHCO_3$ | sodium hydrogen carbonate |
| $NaHCO_3$ | sodium bicarbonate |
| $NaH_2PO$ | sodium hydrogen phosphate |
| NaOH | sodium hydroxide |
| $Na_2SO_4$ | sodium sulphate |
| $NH_4Cl$ | ammonium chloride |
| NMR | nuclear magnetic resonance |
| $O_2$ | oxygen |
| oPT | o-phthaldialdehyde |
| Pd | palladium |
| RT | room temperature |
| $^tBuOH$ | tert butanol |
| $^tBuOK$ | potassium tert butoxide |
| S.E.M. | standard error of mean |
| THF | tetrahydrofuran |
| TLC | thin layer chromatography |
| μl | microliters |
| Triflic Acid | trifluoromethanesulfonic acid |
| TMS Triflate | trimethyl silyl trifluoromethanesulfonate |
| v/v | volume per volume |
| w/v | weight per volume |
| $ZnI_2$ | zinc iodide |
| $\lambda_{em}$ | emission wavelength |
| $\lambda_{2ex}$ | excitation wavelength |

APPENDIX 2

7C1 1-(2-hydroxyethoxycyclopentyl))-indan-2-one
7C2 1-(cyclopentylidene)-indan-2-one
7C3 3-(N-cyclopentylamino)-indan-1-one
7C4 3-(N-cyclopentylamino)-indan-1-one. Hydrochloride
7C5 3-(N-cyclopentyl-N-methylamino)-indan-1-one
7C6 3-(N-cyclopentyl-N-prop-2-enylamino)-indan-1-one
7C7 3-(N-cyclopentyl-N-benzylamino)-indan-1-one
7C8 N-cyclopentyl-N-3-indan-1-onyl-p-toluenesulfonamide
7C9 N-cyclopentyl-N-3-indan-1-onyl ethanamide
7C10 3-(N-cyclopentyl-N-methylamino)-indan-1-one hydrochloride
8C1 2-(2-(methoxycyclopentyl))-indan-1-one
8C2 2-((2-hydroxyethoxy)cyclopentyl))-indan-1-one
8C3 2-(cyclopenten-1-yl)-2-benzylindan-1-one
8C4 2-(cyclopent-1-enyl)-2-benzylindan-1-ol
8C5 2-benzyl-2-cyclopent-1-enyl indan-1-acetoxy

What is claimed is:
1. A compound of one of the formula:

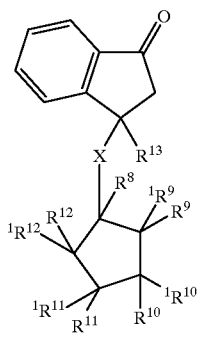

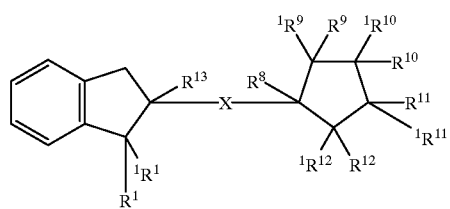

wherein X is a bond or NR wherein R is H, acyl, alkyl, allyl, benzyl or a sulphonate group,
in Formula 7 each of $R^8$, $R^9$, $^1R^9$, R10, $^1R^{10}$, $R^{11}$, $^1R^{11}$, $R^{12}$, $^1R^{12}$ and $R^{13}$ and in Formula 8 each of $R^8$, $R^9$, $^1R^9$, $R^{10}$, $^1R^{10}$, $R^{11}$, $^1R^{11}$, $R^{12}$, $^1R^{12}$ and $R^{13}$ is a member independently selected from the group consisting of H, halo, hydroxy, alkoxy, aryloxy, acetoxy, carboxy, alkyl carbonyl, hydro, carbonyl, amino, amido, alkylamino, hydroxylamino, optionally-substituted and optionally unsaturated $C_1$–$C_{10}$ alkyl, and optionally substituted and optionally unsaturated $C_8$–$C_8$ cycloalkyl,
in Formula 8, $R^1$, $^1R^1$ represents H, OH; OAc,
in Formula 7 any one or more pairs of $R^9$, $^1R^9$; $R^{10}$, $^1R^{10}$; $R^{11}$, $^1R^{11}$; $R^{12}$; $^1R^{12}$ optionally together represent oxo, and
in Formula 8 any one or more of $R^1$, $^1R^1$; $R^9$, $^1R^9$; $R^{10}$, $R^1R^{10}$; $R^{11}$, $^1R^{11}$; $R^{12}$, $^1R^{12}$ optionally together represent oxo; or
a pharmacologically acceptable salt, ester, amide, solvate or isomer thereof.

2. A compound as claimed in claim 1 wherein each alkyl or cycloalkyl is independently substituted with one or more of the same or different members selected from the group consisting of halo, oxo, hydroxy, alkoxy, aryloxy, acetoxy, carboxy, carbonyl, amino, amido, alkylamino, hydroxylamino.

3. A compound as claimed in claim 1 wherein in Formula 7 $R^{10}$, $^1R^{10}$ and/or $R^{11}$, $^1R^{11}$ represent hydrogen.

4. A compound as claimed in claim 1 wherein in Formula 7 $R^{13}$ represents benzyl.

5. A compound as claimed in claim 1 wherein in Formula 7 $R^8$ and $R^9$ or $R^8$ and $R^{12}$ together represent a double bond.

6. A compound as claimed in claim 1 wherein in Formula 7 X is NR.

7. A compound as claimed in claim 6 wherein X represents N substituted by an alkyl group.

8. A compound as claimed in claim 1 wherein in Formula 8 each of $R^{11}$ and $^1R^{11}$ and/or each of $R^{12}$ and $^1R^{12}$ represent hydrogen.

9. A compound as claimed in claim 1 wherein in Formula 8 $R^8$ and $R^9$ or $R^8$ and $R^{12}$ together represent a double bond.

10. A compound as claimed in claim 1 wherein in Formula 8 $R^1$, $^1R^1$ represents H, OH.

11. A compound as claimed in claim 1 wherein in Formula 8 $R^1$, $^1R^1$ represent OAc.

12. A compound as claimed in claim 1 wherein in Formula 8 $R^{13}$ represents benzyl.

13. A compound as claimed in claim 1 wherein in Formula 8 X represents a bond.

14. A compound as claimed in claim 1 wherein in Formula 8 $R^1$, $^1R^1$ together represent O.

15. A compound selected from the group consisting of
3-(N-cyclopentylamino)-indan-1-one,
3-(N-cyclopentylamino)-indan-1-one Hydrochloride,
3-(N-cyclopentyl-N-methylamino)-indan-1-one,
3-(N-cyclopentyl-N-prop-2-enylamino)-indan-1-one,
3-(N-cyclopentyl-N-benzylamino)-indan-1-one,
N-cyclopentyl-N-3-indan-1-onyl-p-toluensulfonamide,
N-cyclopentyl-N-3-indan-1-onyl ethanamide,
3-(N-cyclopentyl-N-methylamino)-indan-1-one hydrochloride,
2-(2-(methoxycyclopentyl))-indan-1-one,
2-((2-hydroxyethoxy)cyclopentyl)-indan-1-one,
2-(cyclopenten-1-yl)-2-benzylindan-1-one,
2-(cyclopent-1-enyl)-2-benzylindan-1-ol, and
2-benzyl-2-cyclopent-1-enyl indan-1-acetoxy.

16. A pharmaceutical composition comprising a compound of Formula 7 or 8 as defined in claim 1 and a pharmaceutically acceptable carrier.

17. A method of prophylaxis or treatment to achieve smooth muscle relaxing activity and/or mast cell stabilizing activity and/or anti-inflammatory activity, which comprises administering an effective amount of a compound of Formula 7 or 8 as defined in claim 1 to a subject in need of such therapy.

18. A compound of the formula:

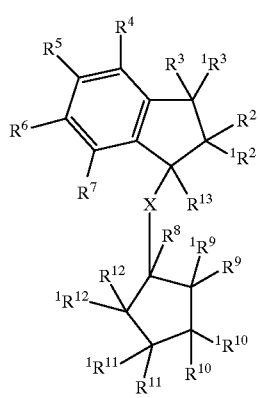

7 wherein one of $R^2$ and $^1R^2$ is H and the other is OH,
each of $R^3$, $^1R^3$, $R^4$, $R^5$, $R^6$, $R^7$, $R^8$, $R^9$, $^1R^9$, $R^{10}$, $^1R^{10}$, $R^{11}$, $^1R^{11}$, $R^{12}$, $^1R^{12}$ and $R^{13}$ is independently a member selected from the group consisting of H, halo, hydroxy, alkoxy, aryloxy, acetoxy, carboxy, alkyl carbonyl, hydro carbonyl, amino, amido, alkylamino, hydroxylamino, optionally substituted and optionally unsaturated $C_1$–$C_{10}$ alkyl, and optionally substituted and optionally unsaturated $C_3$–$C_8$ cycloalkyl, X is a bond or NR, wherein R is H, acyl, alkyl, allyl, benzyl or a sulphonate group, when X is a bond, any pair of $R^8$ and $R^{13}$; $R^8$ and $R^{12}$; or $R^8$ and $R^9$ optionally forms a double bond, and any one or more of $R^3$, $^1R^3$; $R^9$, $^1R^9$; $R^{10}$, $^1R^{10}$; $R^{11}$, $^1R^{11}$; $R^{12}$, $^1R^{12}$, optionally together represent oxo; or
a pharmacologically acceptable salt, ester, amide, solvate or isomer thereof.

19. A compound of the formula:

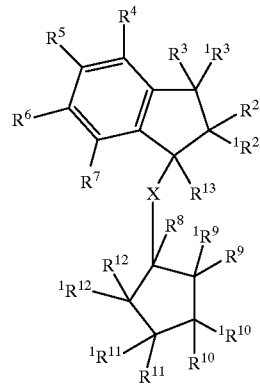

7 wherein each of $R^2$, $^1R^2$, $R^3$, $^1R^3$, $R^4$, $R^5$, $R^6$, $R^7$, $R^8$, $R^9$, $^1R^9$, $R^{10}$, $^1R^{10}$, $R^{11}$, $^1R^{11}$, $R^{12}$, $^1R^{12}$ and $R^{13}$ is a member selected from the group consisting of H, halo, hydroxy, alkoxy, aryloxy, acetoxy, carboxy, alkyl carbonyl, hydro carbonyl, amino, amido, alkylamino, hydroxylamino, optionally substituted and optionally unsaturated $C_1$–$C_{10}$ alkyl, and optionally substituted and optionally unsaturated $C_3$–$C_8$ cycloalkyl, wherein X represents N substituted by an alkyl group, and
any one or more of $R^2$, $^1R^2$, $R^3$, $^1R^3$, $R^9$, $^1R^9$, $R^{10}$, $^1R^{10}$, $R^{11}$, $^1R^{11}$, $R^{12}$, $^1R^{12}$ are optionally oxo; or
a pharmacologically acceptable salt, ester, amide, solvate or isomer thereof.

20. A compound of the formula:

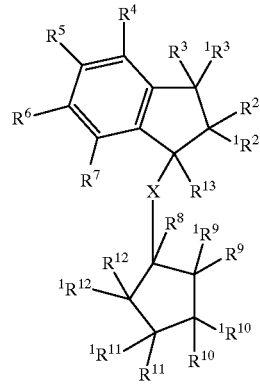

7 wherein $R^2$ and $^1R^2$ together represent oxo, each of $R^3$, $^1R^3$, $R^4$, $R^5$, $R^6$, $R^7$, $R^8$, $R^9$, $^1R^9$, $R^{10}$, $^1R^{10}$, $R^{11}$, $^1R^{11}$, $R^{12}$, $^1R^{12}$ and $R^{13}$ is a member selected from the group consisting of H, halo, hydroxy, alkoxy, aryloxy, acetoxy, carboxy, alkyl carbonyl, hydro carbonyl, amino, amido, alkylamino, hydroxylamino, optionally substituted and optionally unsaturated $C_1$–$C_{10}$ alkyl, and optionally substituted and optionally unsaturated $C_3$–$C_8$ cycloalkyl, X is a bond or NR, wherein R is H, acyl, alkyl, allyl, benzyl or a sulphonate group, when X is a bond, any pair of $R^8$ and $R^{13}$; $R^8$ and $R^{12}$; or $R^8$ and $R^9$ optionally together forms a double bond, and any one or more pairs of $R^3$, $^1R^3$; $R^9$, $^1R^9$; $R^{10}$, $^1R^{10}$, $R^{11}$, $^1R^{11}$; $R^{12}$, $^1R^{12}$ optionally together are oxo; or a pharmacologically acceptable salt, ester, amide, solvate or isomer thereof.

21. A compound of the formula:

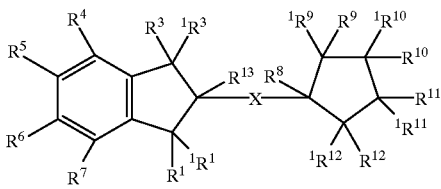

wherein $R^{13}$ represents benzyl, each of $R^1$, $^1R^1$, $R^3$, $^1R^3$, $R^4$, $R^5$, $R^6$, $R^7$, $R^8$, $R^9$, $^1R^9$, $R^{10}$, $^1R^{10}$, $R^{11}$, $^1R^{11}$, $R^{12}$ and $^1R^{12}$ is a member selected from the group consisting of H, halo, hydroxy, alkoxy, aryloxy, acetoxy, carboxy, alkyl carbonyl, hydro carbonyl, amino, amido, alkylamino, hydroxylamino, optionally substituted and optionally unsaturated $C_1$–$C_{10}$ alkyl, and optionally substituted and optionally unsaturated $C_3$–$C_8$ cycloalkyl, X is a bond or NR, wherein R is acyl, alkyl, allyl, benzyl or a sulphonate group, when X is a bond, any pair of $R^8$ and $R^{12}$, or $R^8$ and $R^9$ together optionally forms a double bond, and each pair of $R^1$, $^1R^1$; $R^3$, $^1R^3$; $R^9$, $^1R^9$; $R^{10}$, $^1R^{10}$; $R^{11}$, $^1R^{11}$; $R^{12}$, $^1R^{12}$ together optionally represents oxo; or a pharmacologically acceptable salt, ester, amide, solvate or isomer thereof.

22. A compound of the formula:

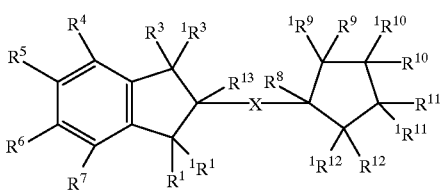

wherein each of $R^1$, $^1R^1$, $R^3$, $^1R^3$, $R^4$, $R^5$, $R^6$, $R^7$, $R^8$, $R^9$, $^1R^9$, $R^{10}$, $^1R^{10}$, $R^{11}$, $^1R^{11}$, $R^{12}$, $^1R^{12}$ and $R^{13}$ is a member selected from the group consisting of H, halo, hydroxy, alkoxy, aryloxy, acetoxy, carboxy, alkyl carbonyl, hydro carbonyl, amino, amido, alkylamino, hydroxylamino, optionally substituted and optionally unsaturated $C_1$–$C_{10}$ alkyl, and optionally substituted and optionally unsaturated $C_3$–$C_8$ cycloalkyl, X represents N substituted by an alkyl group, each pair of $R^1$, $^1R^1$; $R^3$, $^1R^3$; $R^9$, $^1R^9$; $R^{10}$, $^1R^{10}$; $R^{11}$, $^1R^{11}$; $R^{12}$, $^1R^{12}$ together optionally represents oxo; or a pharmacologically acceptable salt, ester, amide, solvate or isomer thereof.

23. A compound of the formula:

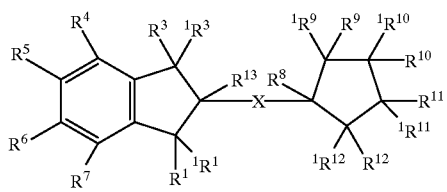

wherein each of $R^1$, $^1R^1$, $R^3$, $^1R^3$, $R^4$, $R^5$, $R^6$, $R^7$, $R^8$, $R^9$, $^1R^9$, $R^{10}$, $^1R^{10}$, $R^{11}$, $^1R^{11}$, $R^{12}$ and $^1R^{12}$ is a member selected from the group consisting of H, halo, hydroxy, alkoxy, aryloxy, acetoxy, carboxy, alkyl carbonyl, hydro carbonyl, amino, amido, alkylamino, hydroxylamino, optionally substituted and optionally unsaturated $C_1$–$C_{10}$ alkyl, and optionally substituted and optionally unsaturated $C_3$–$C_8$ cycloalkyl, wherein X represents a double bond, and each pair of $R^1$, $^1R^1$; $R^3$, $R^1R^3$; $R^9$, $^1R^9$; $R^{10}$, $^1R^{10}$; $R^{11}$, $^1R^{11}$; $R^{12}$, $^1R^{12}$ together optionally represents oxo; or a pharmacologically acceptable salt, ester, amide, solvate or isomer thereof.

24. A process for preparing a compound of one of the formulae

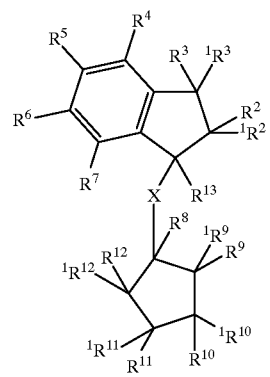

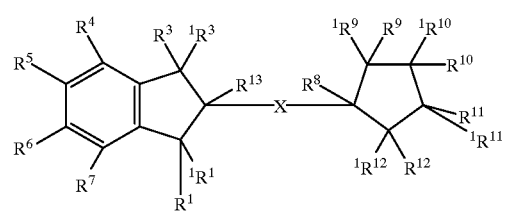

wherein in Formula 7 each of $R^2$ to $R^{13}$ and in Formula 8 each of $R^1$ and $R^3$ to $R^{13}$ is a member selected from the group consisting of H, halo, hydroxy, alkoxy, aryloxy, acetoxy, carboxy, alkyl carbonyl, hydro carbonyl, amino, amido, alkylamino, hydroxylamino, an amine oxide group, an azo group, cyano, a hydrazino group, a hydrazide group, a hydrazone group, an imide group, an iminoether group, a ureyl group, oxime, nitro, nitrate, nitrite, a nitroso group, nitrile, a heterocyclic group containing one or more of N, O of S, an aralkyl group, a mono or polybenzoid aryl group, a substituted aryl group, thiol, thioureyl, a phenylthio group, a sulphonic acid group, a sulphoxide group, a sulphone group, optionally substituted and optionally unsaturated alkyl containing 1 to 10 carbon atoms, and optionally substituted and optionally unsaturated cycloalkyl containing 3 to 8 carbon atoms;

X is a bond, O, or NR (wherein R is acyl, alkyl or a sulphonate group), S, SO or $SO_2$ when X is a bond any pair of: $R^8$ and $R^{13}$; $R^8$ and $R^{12}$; or $R^8$ and $R^9$ optionally together represents a double bond, in formula 7 any one or more pairs of $R^2$, $^1R^2$; $R^3$, $^1R^3$; $R^9$, $^1R^9$; $R^{10}$, $^1R^{10}$; $R^{11}$, $^1R^{11}$; $R^{12}$, $^1R^{12}$ optionally together represent oxo, and in formula 8 any one or more pairs of $R^1$, $^1R^1$; $R^3$, $^1R^3$; $R^9$, $^1R^9$; $R^{10}$, $^1R^{10}$; $R^{11}$, $^1R^{11}$; $R^{12}$, $^1R^{12}$ optionally together represent oxo; or a pharmacologically acceptable salt, ester, amide, solvate or isomer thereof by a) reacting Indan-1-one with aluminum tri-tert-butoxide, b) alkylation of an α, β, enone to give an α-alkyl-β enone, c) reduction of a double bond and/or a ketone functional group, d) reduction of a ketone functional group by using sodium borohydride, e) reduction of a ketone functional group using hydrazine hydrate, f) reduction of ketone functional group using sodium cyanoborohydride, g) reduction or isomerisation of the α, β enone double bond with 5% Palladium on activated carbon, h) reduction of a C=C outside the five membered ring using Wilkinsons catalyst, i) coupling a silyl enol ether of an indanone with a corresponding dimethyl acetal of the same or a different indanone using a Lewis acid, j) coupling of an 3-bromo indan-1-one to a silyl enol ether using a Lewis acid, k) reduction of a ketone functional group with lithium tritertbutoxyaluminohydride or by using lithium aluminium hydride as reducing agent, l) coupling of a silyl enol-ether of an idanone with the corresponding cyclic ketal of a 1-indanone or any suitable carbonyl compound using a Lewis acid, m) coupling of a 3-bromo-indanone to 1 to 2-amino-indan derivatives, n) self coupling of a 1-indanol derivative using methane sulphonic chloride or methane sulphonic anhydride, o) acetylation of an alcohol functional group of a compound of formula 7 or of formula 8, or p) forming an oxime with either pyridine or sodium acetate as base.

25. A process as defined in claim 24 wherein alkylation step (b) is effected with lithium diisopropylamino or with potassium tert-butoxide; reduction step (c) is catalytically effected with paladium over activated charcoal and which optionally also includes concentrated aqueous HCl; the Lewis acid of coupling step (i) is TMS Triflate; the coupling step optionally includes eliminating methanol from the resulting methyl ethers generated from the coupling of the silyl enol ethers and dimethyl acetals of different indanones, and methanol is optionally eliminated by adding Triflic acid; the Lewis acid in each of steps (j) and (l) is TMS Triflate; coupling step (m) includes the step of N-alkylation or N-acylation of coupled products; and oxime-forming step (p) is effected with hydroxylamine hydrochloride, optionally including the step of O-alkylation of an oxime functional group with either potassium tert-butoxide or lithium diisopropylamide as base, and optionally further including the step of α-alkylation of the benzyl oxime ether using N-butyl lithium as base and further optionally including reduction of the O-benzyl oxime ethers using lithium aluminumhydride as reducing agent.

* * * * *